United States Patent
Holloway

(10) Patent No.: US 10,347,155 B2
(45) Date of Patent: Jul. 9, 2019

(54) SUTURING TRAINING DEVICE AND METHOD

(71) Applicant: UTI Limited Partnership, Calgary (CA)

(72) Inventor: Daniel Holloway, Calgary (CA)

(73) Assignee: UTI LIMITED PARTNERSHIP, Calgary (CA)

(*) Notice: Subject to any disclaimer, the term of this patent is extended or adjusted under 35 U.S.C. 154(b) by 371 days.

(21) Appl. No.: 15/242,003

(22) Filed: Aug. 19, 2016

(65) Prior Publication Data

US 2017/0053563 A1 Feb. 23, 2017

Related U.S. Application Data

(60) Provisional application No. 62/207,464, filed on Aug. 20, 2015.

(51) Int. Cl.
*A61B 17/04* (2006.01)
*G09B 23/28* (2006.01)
*G09B 23/30* (2006.01)

(52) U.S. Cl.
CPC .......... *G09B 23/28* (2013.01); *A61B 17/0469* (2013.01); *G09B 23/30* (2013.01)

(58) Field of Classification Search
CPC .................................................. A61B 17/0469
See application file for complete search history.

(56) References Cited

U.S. PATENT DOCUMENTS

| | | | | |
|---|---|---|---|---|
| 4,789,340 A * | 12/1988 | Zikria | ..................... | G09B 23/28 434/262 |
| 5,380,207 A * | 1/1995 | Siepser | ................... | G09B 23/30 434/270 |
| 5,403,191 A * | 4/1995 | Tuason | ................. | G09B 23/285 434/262 |
| 5,873,732 A * | 2/1999 | Hasson | ................. | G09B 23/286 434/262 |
| 5,951,301 A * | 9/1999 | Younker | .............. | G09B 23/285 434/268 |

(Continued)

*Primary Examiner* — Eddy Saint-Vil
*Assistant Examiner* — William D Ermlick
(74) *Attorney, Agent, or Firm* — Billion & Armitage; Michael A. Collins

(57) ABSTRACT

An apparatus for training suturing techniques. The apparatus comprises: (i) a suturing cartridge presentation display with a first receptacle for demountably engaging therein a first suturing cartridge and a second receptacle for demountably engaging therein a second suturing cartridge, (ii) a microprocessor, a graphical user interface, and at least one software program for cooperating with the microprocessor for training, monitoring, reporting suturing techniques; and (iii) a housing for mounting therein the suturing cartridge presentation display, the microprocessor, and the graphical user interface. Each receptacle is associated with a pressure sensor and a plurality of LEDs. The suturing cartridges are fillable with semi-solid, resilient material into which suturing instruments may be inserted and withdrawn. The pressure sensors detect movements associated with manipulation of suturing instruments, while the LEDs provide guidance to suturing tasks and visual cues relating to acceptable and unacceptable manipulation of suturing instruments.

17 Claims, 9 Drawing Sheets

(56) References Cited

U.S. PATENT DOCUMENTS

| | | | | |
|---|---|---|---|---|
| 7,963,770 B2 * | 6/2011 | Kukora | G09B 23/285 | 434/262 |
| 8,073,528 B2 * | 12/2011 | Zhao | B25J 9/1689 | 600/424 |
| 2004/0142314 A1 * | 7/2004 | Hasson | G09B 23/285 | 434/262 |
| 2005/0142525 A1 * | 6/2005 | Cotin | G09B 23/285 | 434/262 |
| 2007/0166682 A1 * | 7/2007 | Yarin | G09B 23/285 | 434/267 |
| 2007/0238081 A1 * | 10/2007 | Koh | G09B 23/285 | 434/262 |
| 2008/0064017 A1 * | 3/2008 | Grundmeyer, III | G09B 23/28 | 434/262 |
| 2010/0009329 A1 * | 1/2010 | Takanishi | A61B 17/00 | 434/262 |
| 2010/0035222 A1 * | 2/2010 | Kukora | G09B 23/28 | 434/262 |
| 2011/0281251 A1 * | 11/2011 | Mousques | G09B 23/283 | 434/274 |
| 2012/0115117 A1 * | 5/2012 | Marshall | G09B 23/28 | 434/262 |
| 2012/0115118 A1 * | 5/2012 | Marshall | G09B 23/28 | 434/262 |
| 2013/0101973 A1 * | 4/2013 | Hoke | G09B 23/34 | 434/267 |
| 2014/0051049 A1 * | 2/2014 | Jarc | G09B 23/30 | 434/267 |
| 2014/0248596 A1 * | 9/2014 | Hart | G09B 23/30 | 434/272 |
| 2014/0349265 A1 * | 11/2014 | Park | G09B 23/32 | 434/272 |
| 2015/0086955 A1 * | 3/2015 | Poniatowski | G09B 23/28 | 434/267 |
| 2015/0320419 A1 * | 11/2015 | Gorek | A61B 17/06161 | 206/366 |
| 2016/0063898 A1 * | 3/2016 | Bernal | G09B 23/32 | 434/271 |
| 2018/0116724 A1 * | 5/2018 | Gmeiner | A61B 34/10 | |

* cited by examiner

SUTURING TRAINING DEVICE AND METHOD

CROSS-REFERENCE TO RELATED APPLICATIONS

This application claims priority to U.S. Provisional Application No. 62/207,464, filed on Aug. 20, 2015, and entitled "SUTURING TRAINING DEVICE AND METHOD" the disclosure of which is incorporated by reference in its entirety.

TECHNICAL FIELD

This disclosure relates devices for teaching surgical skills. More specifically, this disclosure pertains devices and apparatus for teaching and practicing suturing techniques and skills to medical personnel.

BACKGROUND

Surgical procedures are technically demanding and require precise placement of sutures for successful healing of wound closures. A variety of different types of sutures must be placed during technically challenging surgical procedures on sites within a patient's body cavity and/or within their skeletal framework wherein a target surgical site may situated in challenging orientations and with limited access for surgical implements. Surgical trainees must acquire the skills necessary to perform precise suturing under these challenging conditions.

Currently, suturing skills are taught through trainee observation of surgical procedures being performed on patients in operating rooms accompanied with some hands-on supervised suturing of more easily accessed and visible wound sites. Training also includes the teaching of surgery procedures using various surgical instruments and techniques with low-fidelity simulators exemplified by silicone pads, and/or through the use of animal models such as porcine tissue. The limitation of the current simulation devices available in the laboratory is that they are intended to teach the basic suturing skills. There aren't any commonly used suture training devices available which enable trainees to learn and practice the more advanced skills in a consistent and repeatable manner. A surgical trainee needs to develop and practice suturing skills at challenging angles and orientations because they will encounter these scenarios in the operating room.

SUMMARY

The embodiments of the present disclosure pertain to an apparatus and its components for use in teaching suturing techniques to medical practitioners and trainees, for the practice of suturing techniques, and for providing feedback to the user regarding their execution of the suturing techniques.

According to one embodiment of the present disclosure, the suturing training apparatus generally comprises: (i) a spherical presentation display having a plurality of receptacles for demountable engagement therein of suturing cartridges, (ii) electronic components comprising a microprocessor and a graphical user interface for communicating with the spherical presentation display and a user, and (iii) a housing for containing therein the spherical presentation display and the electronic components.

According to one aspect, the spherical presentation display may comprise a plurality of receptacles for demountable engagement of circular suturing cartridges. Another aspect relates to a plurality of receptacles for demountable engagement of a plurality of diamond-shaped suturing cartridges. Yet another aspect relates to a spherical presentation display wherein the uppermost receptacle is configured for demountable engagement of a circular suturing cartridge and a plurality of diamond-shaped receptacles are equidistantly spaced-apart in a planar circumference underneath the uppermost circular receptacle. It is optional for the Another embodiment pertains to the suturing cartridges disclosed herein. The cartridges generally comprise containers for receiving therein a soft, semi-solid, resilient material for insertion thereinto of suturing instruments. According to one aspect, different stiffness of semi-solid resilient material may be provided into different cartridges to simulate different resistances to penetration of suturing instruments during performance of surgical procedures. According to another aspect, a film material may be provided on top of a semi-solid, resilient material contained within a cartridge, to simulate resistance of serous membranes to penetration by suturing instruments.

Another embodiment pertains to pressure sensors cooperating with the receptacles in spherical presentation display and/or with the suturing cartridges, for detection of insertions into, movements within and withdrawal of suturing instruments into, within and from the suturing cartridges. The motion data detected by the pressure sensors is communicated to a microprocessor which assesses and compares the motion data to suturing reference standards, and generates signals conveyed to LEDs positioned in the spherical presentation display about the target cartridge with lights that indicate that the suturing motions are within acceptable parameters or are outside of acceptable parameters. According to one aspect, the microprocessor is programmable to generate reporting data pertaining to time taken to perform a suturing technique, a visual record of the suture produced by the detected suturing instrument motions, and suturing performance summaries. According to another aspect, the microprocessor is interactive with a graphical user display to enable a user or a trainee or a practitioner to select a suturing training exercise and to monitor their progress in developing manual dexterity and expertise.

BRIEF DESCRIPTION OF THE FIGURES

The present disclosure will be described in conjunction with reference to the following drawings in which.

DETAILED DESCRIPTION

Figure 1:
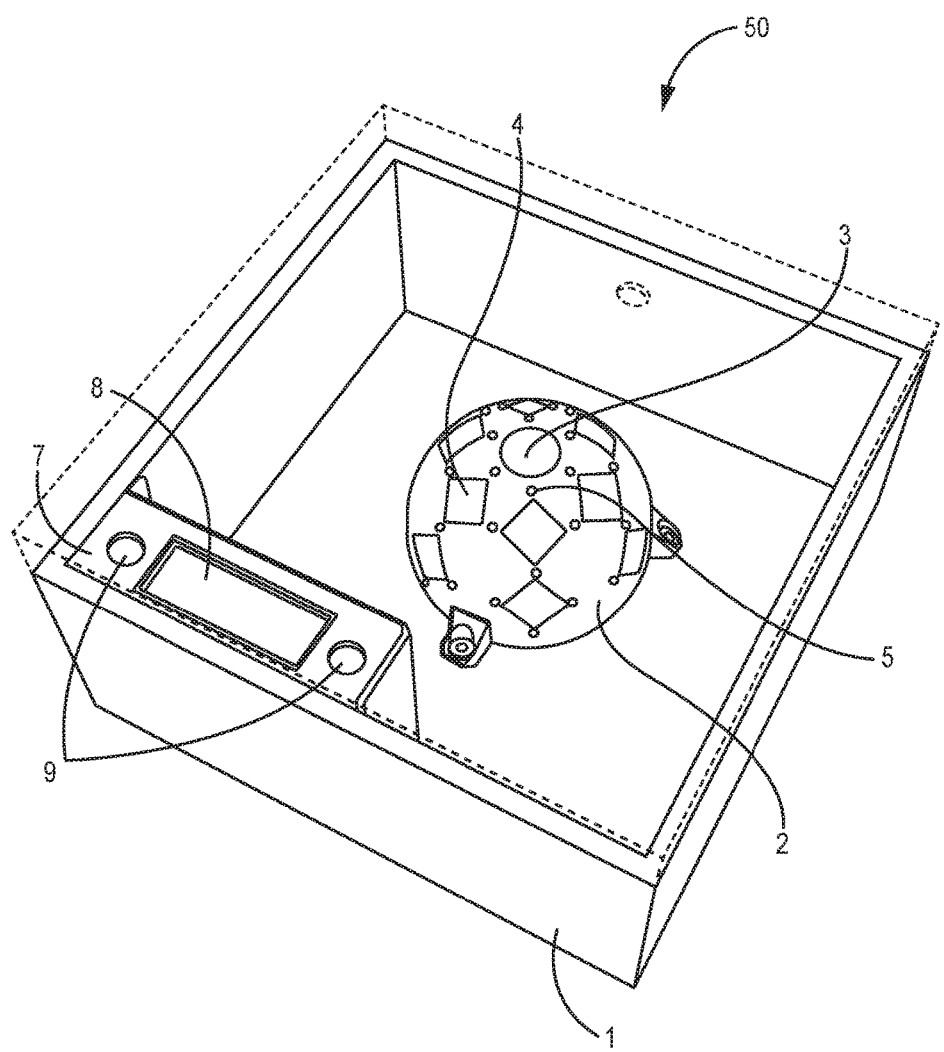
FIG. 1 is a perspective view of a suturing training device according to an embodiment of the present disclosure.

The embodiments of the present disclosure generally pertain to apparatus for use in training suturing techniques to health personnel, practitioners, and trainees.

An example of an apparatus 50 disclosed herein is shown in FIGS. 1-9 and generally comprises an assembly comprising a suturing hemisphere 2 mounted onto a false bottom 18 within a box 1. The suturing hemisphere 2 may be fashioned from a plastic or alternatively wood or alternatively metal or alternatively a resilient polymer and the like. The suturing hemisphere 2 preferably comprises a hollow shell, and is affixed to the false bottom 18 with engagement devices exemplified by screws that secure mounting tabs 6, provided at the base of the suturing hemisphere 2, to the false bottom 18 of the box 1.

The suturing hemisphere 2 is preferably a symmetrical dome in the shape of a sphere cut in half. The diameter of the suturing hemisphere 2 may be 5.0 cm, 7.5 cm, 10.0 cm, 12.5 cm, 15.0 cm, 17.5 cm, 20.0 cm, 22.5 cm, 25.0 cm, 27.5 cm, 30.0, and therebetween. According to one aspect, the suturing hemisphere may be in the shape of a symmetrical dome extending upward from a cylinder wherein the length of the cylinder is 0.5 cm, 1.0 cm, 2.0 cm, 3.0 cm, 4.0 cm, 5.0 cm, and therebetween. According to another aspect, the suturing hemisphere 2 is preferably a symmetrical dome in the shape of the upper 55% portion of a cut sphere or alternatively, the upper 60% portion, 65% portion, 70% portion, 75% portion, and therebetween.

It is to be noted that the suturing hemisphere disclosed herein may also be referred to as a suturing cartridge presentation display. It is within the scope of this disclosure for the suturing cartridge presentation display to be formed into a topographical representation of one or more organs from within a mammalian abdominal cavity, a mammalian thorax, and/or a mammalian thorax-abdominal cavity. For example, the topographical representation may be one or more of a heart, a lung, a stomach, a liver, a gall bladder, a pancreas, a kidney, a bladder, a urethra, an ovary, a fallopian tube, a uterus, or any other organ from a mammalian abdominal cavity, a mammalian thorax, and/or a mammalian thorax-abdominal cavity. The suturing cartridge presentation display may be a topographical representation of one or more human organs. Alternatively, the mammalian display may be a topographical representation of one or more organs from a feline, a canine, an equine, a bovine, a primate, and the like.

The dimensions of the box 1 into which the suturing hemisphere 2 is mounted, are selected to simulate presentation of a surgical target site in a mammalian patient's abdomen or chest cavity. The walls of the box create boundaries which affect the visualization and access to the suturing surfaces. This restriction in visualization and access is similar to the restrictions found when operating inside a chest cavity or another body cavity. When viewed from the top, the box 1 preferably is square-shaped. However, it may also be rectangular if so desired. It is suitable for about 1.0 cm of space to be provided between the inside of each wall of the box and the outermost edges of the suturing hemisphere 2, alternatively 1.5 cm, 2.0 cm, 2.5 cm, 3.0 cm, 3.5 cm, 4.0 cm, 4.5 cm, 5.0 cm of space. Alternatively, the top surface area of the box 1 may be 10% larger than the cross-sectional diameter of the suturing hemisphere 2 at its widest point, 15% larger, 20% larger, 25% larger, 30% larger, 35% larger, 40% larger, 45% larger, 50% larger, 75% larger, 100% larger, and therebetween. The box 1 may additionally comprise a lid (not shown) that may optionally be hinged. The lid, also referred to herein as a coverplate, may be formed from a transparent material such as glass or plastic, for example PLEXIGLAS® (PLEXIGLAS is a registered trademark of Arkema France Corp., Colombes, FR). Two or more access ports may be provided in the transparent lid to allow access therethrough for trocars and/or other instruments used in endoscopic surgical procedures and laparoscopic surgical procedures for training of performance of suturing techniques used in endoscopic surgical procedures and laparoscopic surgical procedures.

Examples of suitable access ports are surgical access ports.

Figure 4:
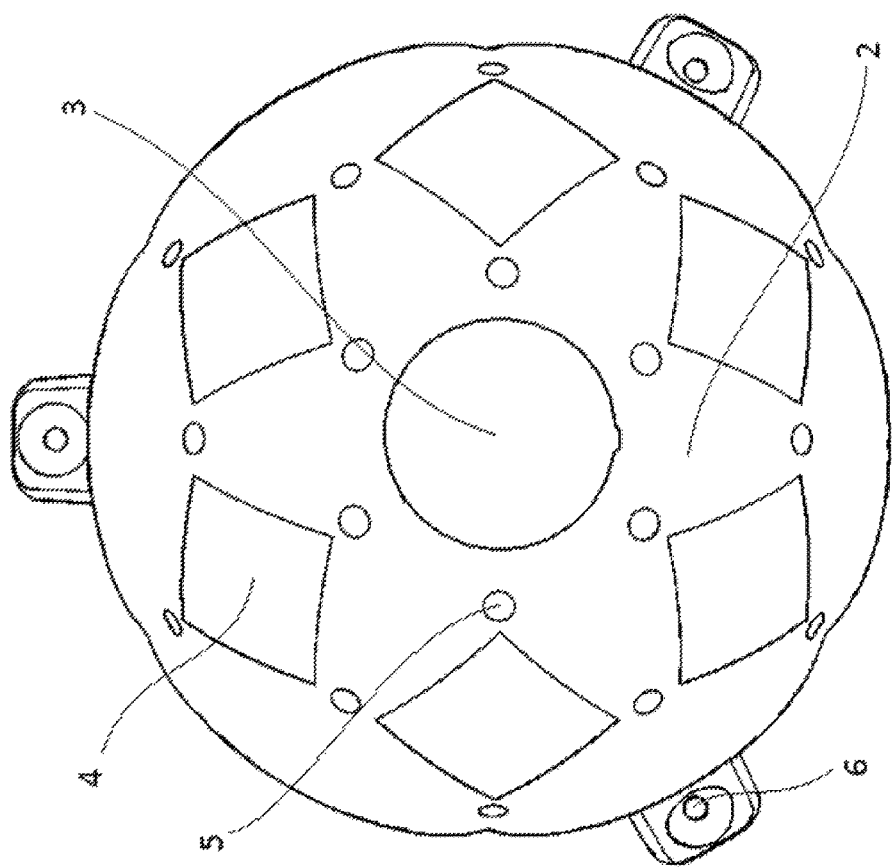
FIG. 4 is a top view of the suturing hemisphere from FIG. 3, shown with the suturing cartridges removed.

The suturing hemisphere 2 is provided with: (i) a circular receptacle 3 for demountably engaging therein a circular suturing cartridge 15, and (ii) a plurality of diamond-shaped receptacles 4 for demountably engaging therein each diamond-shaped receptacle 4 a diamond-shaped suturing cartridge 12. According to one aspect, the circular receptacle 3 is situated at the top of the suturing hemisphere 2 and a first plurality of diamond-shaped receptacles 4 is arranged in a circular pattern around the circumference of the suturing hemisphere 2, wherein the diamond-shaped receptacles 4 equidistantly spaced apart from each other and from the circular receptacle 3, as is best seen in FIG. 4. It is to be noted that suitable alternative shapes for the circular receptacles may be ellipsoid, toroidal, tear drop, amoeboid, and other such continuous curvilinear forms, for demountably engaging cartridges formed to fit therein. Suitable alternative geometric shapes for the diamond-shaped receptacles may be squares, rectangles, parallelograms, triangles, and the like, for demountably engaging cartridges formed to fit therein.

The suturing hemisphere 2 additionally comprises a plurality of multi-colour LED lights 5 wherein a LED light 5 is disposed adjacent each corner of each diamond-shaped receptacle 4 as shown in FIG. 4. This example of a suitable arrangement provides six equidistantly spaced-apart LED lights 5 around the periphery of the circular receptacle 3. Suitable colours emitted by the LED lights 5 are preferably green and red, and may additionally or alternatively include yellow and/or orange. However, other colours may also be used if so desired. A suitable function of the LED lights 5 is to provide guidance for initiating a suture and completing a suture throw, for example, indicating a precise location for placement of a suture throw and/or an angle for initiating the suture throw. For clarity, a suture throw is the process of inserting a needle with a suture into a selected first target location then egressing the needle from a selected second target location. For example, one of the LED lights 5 about a selected receptacle may emit a green light indicating the location where a suture throw should be initiated while an LED light 5 opposite the green-emitting LED light 5, may emit a red light indicating the location where the suture throw should be completed. A different emitted light colour by one of the other LED lights 5, for example yellow or orange, could indicate in which of the receptacles 3, 4, the suture throw should be performed.

It is optional for an apparatus 50 disclosed herein to additionally comprise electronic components housed within the box 1 for detecting pressures applied to various locations about, on, and within the suturing hemisphere 2 during a trainee's execution of a suturing exercise, and for providing instantaneous visual and/or auditory feedback when pressures are detected. Suitable components are exemplified by pressure sensors and/or vibration sensors (not shown) mounted within the suturing hemisphere 2, wiring 17 connecting the sensors with a printed circuit board 11 which is in communication with a microcontroller 10 and the LED lights 5 mounted in the suturing hemisphere 2, a user interface 7 having a display 8 exemplified by a liquid crystal display (LCD) and control buttons 9, said user interface 7 in communication with the microcontroller 10 (FIGS. 1, 9), and a power supply (not shown) in communication with the microcontroller 10. In the apparatus shown in FIGS. 1 and 9, the microcontroller, printed circuit board, and power supply are housed in the box 1 underneath the false bottom 19, while the user interface 7 is mounted on an inner wall of the box 1 such that the display is about the top surface of the box 1.

Figure 2:
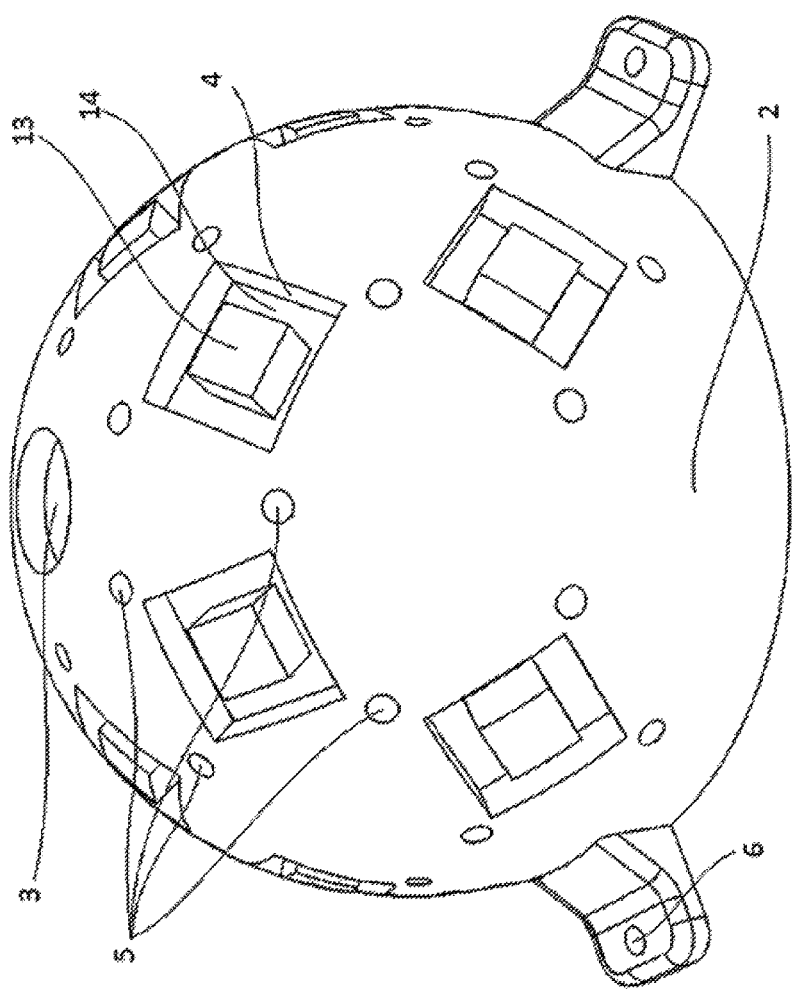
FIG. 2 is a perspective view of a suturing hemisphere from the suturing training device shown in FIG. 1.
Figure 3:
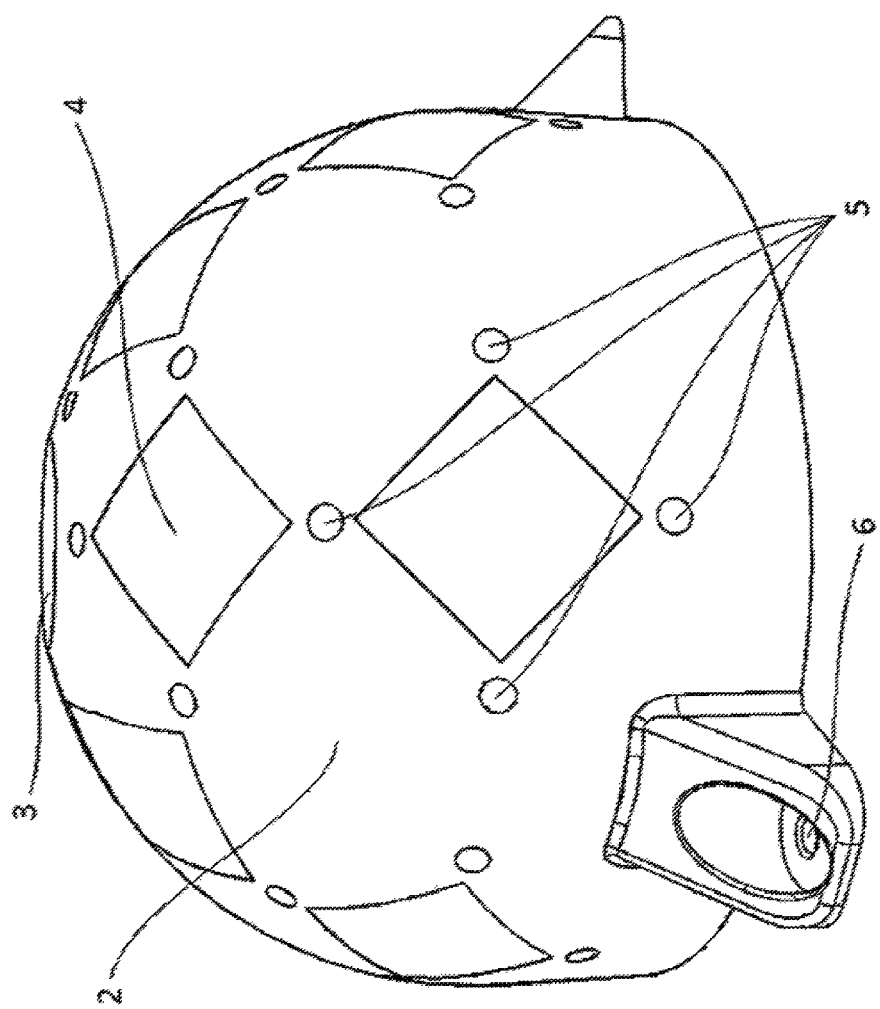
FIG. 3 is a perspective view of the suturing hemisphere from FIG. 2, shown with the suturing cartridges removed.

It is optional, if so desired, to provide a second plurality of diamond-shaped receptacles 4 arranged in an equidistantly spaced-apart circular pattern around the circumference of the suturing hemisphere 2 underneath the first circular arrangement of diamond-shaped receptacles 4, as exemplified in FIGS. 2 and 3. It is also optional if so desired, to provide a plurality of only circular receptacles, or alternatively, a plurality of only diamond-shaped receptacles about the suturing hemisphere. It is within the scope of the present disclosure to substitute other geometric shapes for the diamond-shaped receptacles, for example squares, trapezoids, parallelograms, triangles, and the like. It is also within the scope of the present disclosure to substitute other continuous curvilinear shapes for the circular receptacles, for example ellipses, tear drops, asymmetrical amoeboid shapes, and the like. The suturing hemisphere 2 may also be referred as a "suturing cartridge presentation display".

Figure 5:
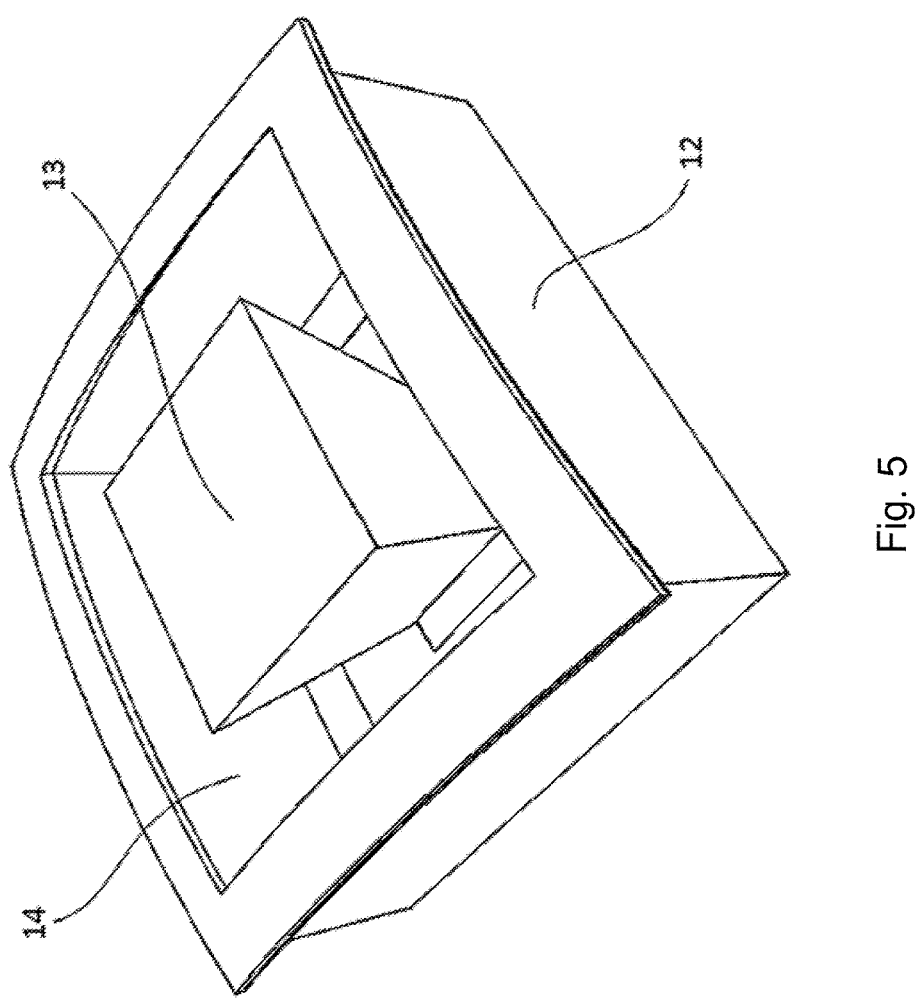
FIG. 5 is a perspective view of a diamond-shaped suturing cartridge according to an embodiment of the present disclosure.
Figure 6:
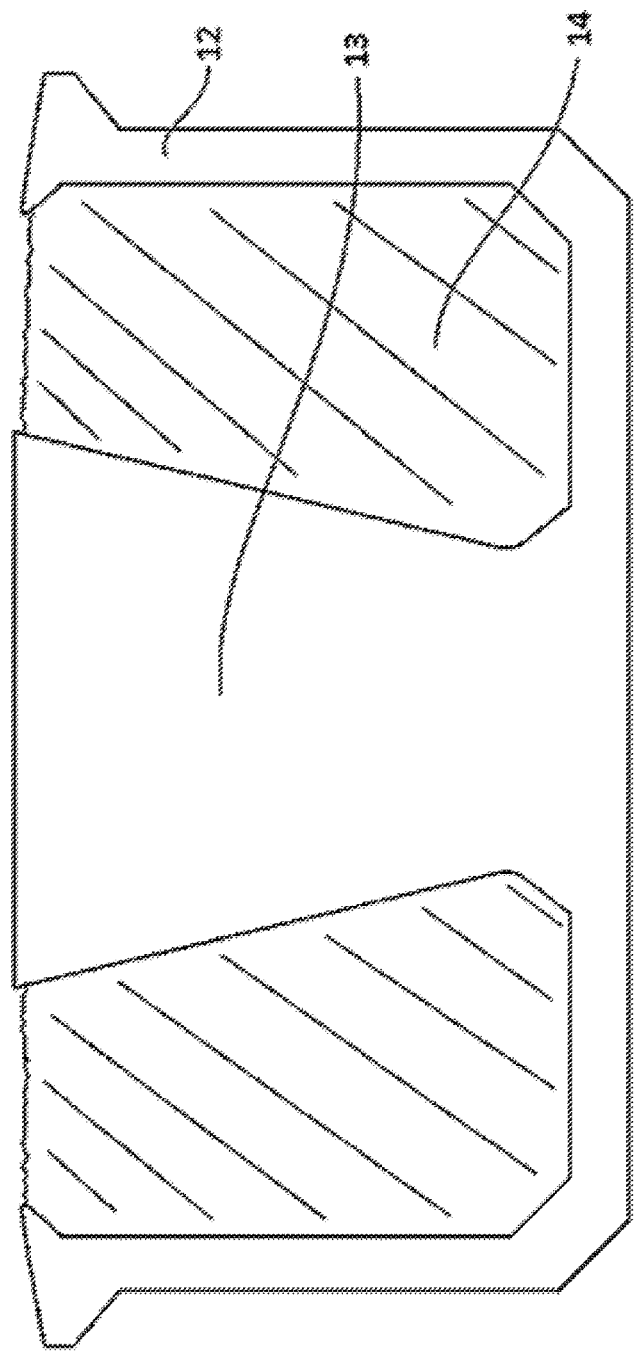
FIG. 6 is a cross-sectional side view of the suturing cartridge shown in FIG. 5.

An example of a diamond-shaped suturing cartridge 12 disclosed herein for demountably engaging a diamond-shaped receptacle 4, is shown in FIGS. 5 and 6 and generally comprises a channel 14 encircling a diamond-shaped centre-post 13. The channel 14 is filled to the top with a soft, semi-solid, resilient material exemplified by silicone and the like. The purpose of the center structure is to prohibit suture needle passage through the middle of the suturing cartridge. A trainee can only pass the suture needle through channels of silicone from one corner of the diamond to another. This restriction of needle passage only through the channels helps enforce precise control of the suture needle. If the trainee was to attempt to pass the suture needle at an incorrect angle, then they will encounter the sidewall or center structure of the suturing cartridge. The suturing cartridges have ridges at the top of the walls and taper from the base to the top in order to help contain the silicone during use. After repeated use for suturing training, the used diamond-shaped suturing cartridge 12 can be disengaged from the diamond-shaped receptacle 4 and replaced with a fresh diamond-shaped suturing cartridge 12. Alternatively, the suturing cartridge may be formed into a square or a trapezoid or a parallelogram or a triangle.

Figure 7:
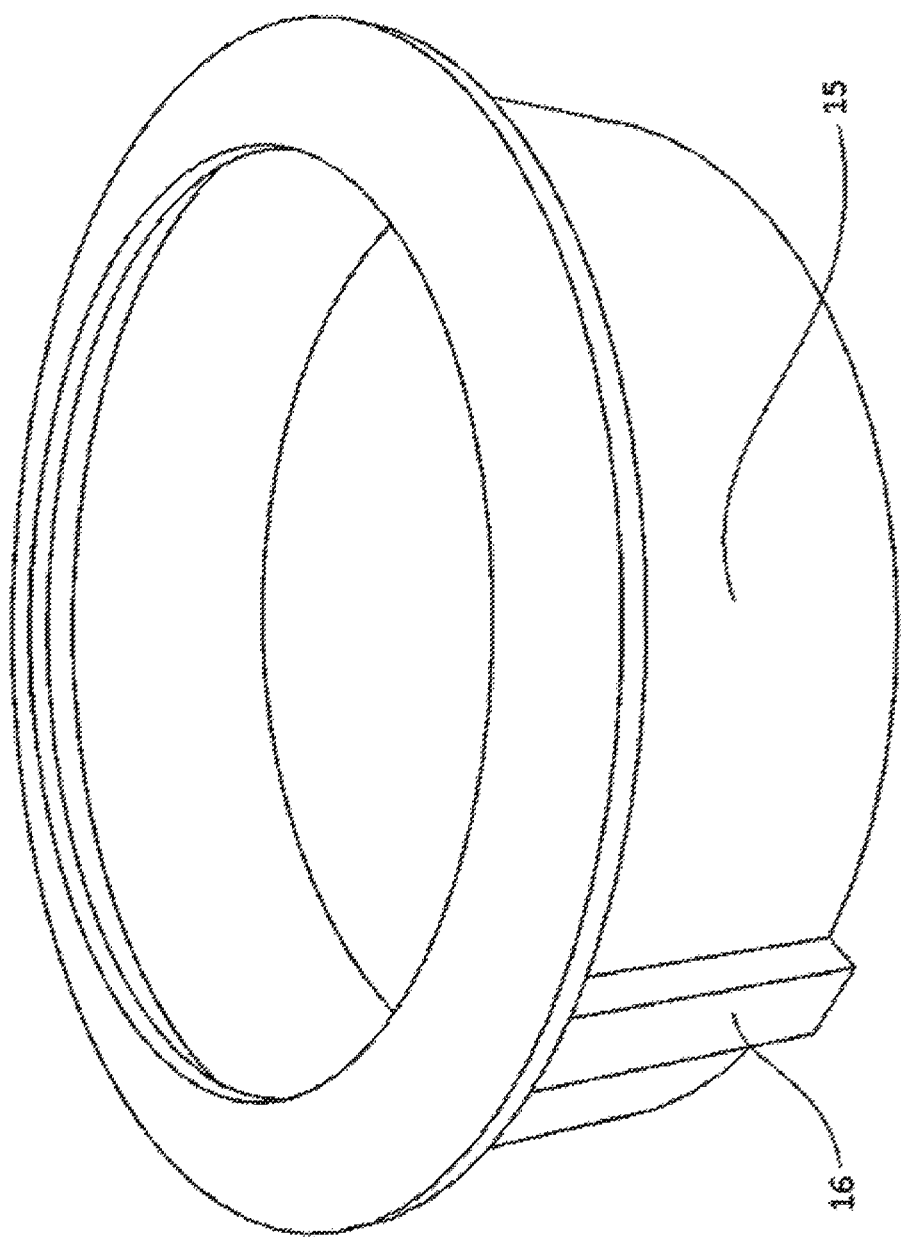
FIG. 7 is a perspective view of a circular suturing cartridge according to an embodiment of the present disclosure.
Figure 8:
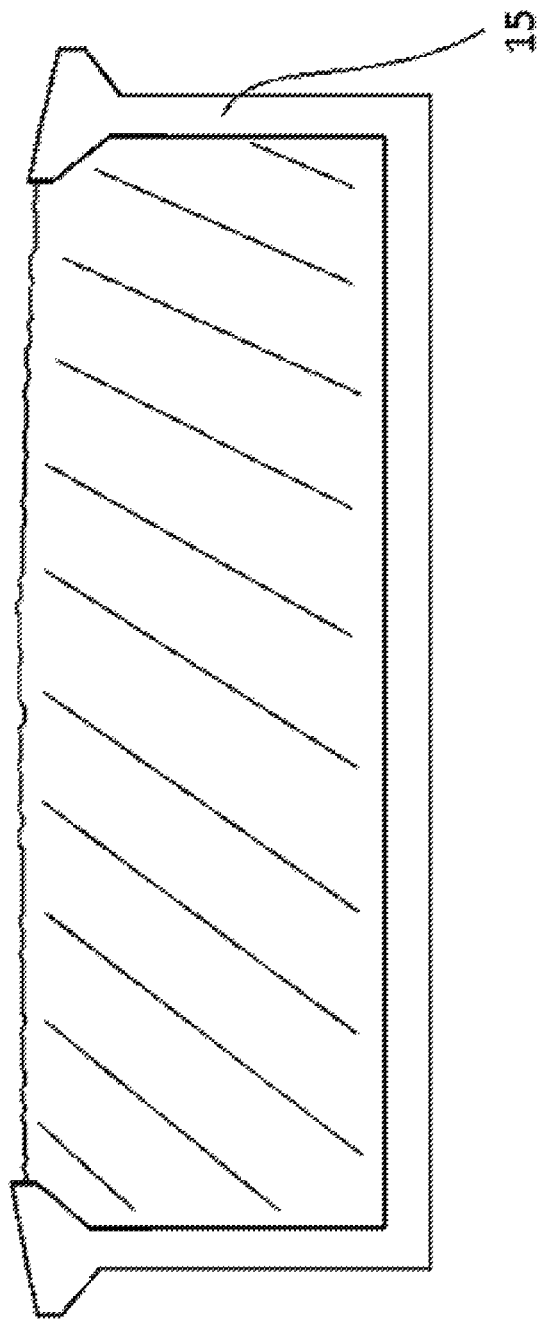
FIG. 8 is a cross-sectional side view of the suturing cartridge shown in FIG. 5.
Figure 9:
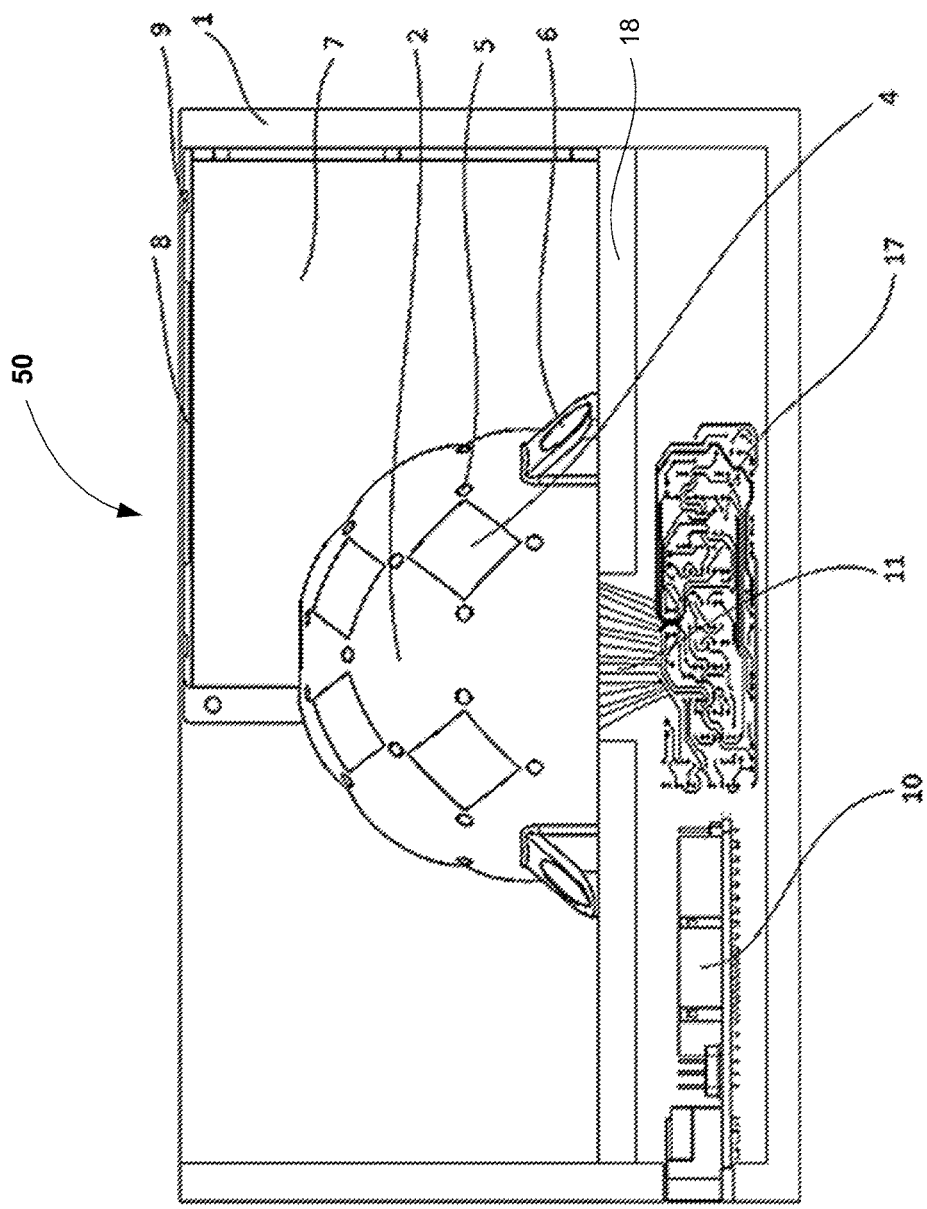
FIG. 9 is a cross-sectional side view of the suturing training device shown in FIG. 1.

An example of a circular suturing cartridge 15 disclosed herein for demountably engaging a circular receptacle 3, is shown in FIGS. 7 and 8. It is suitable to provide the circular suturing cartridge 15 with a keyway 16 for engaging a slot provided therefor in the suturing hemisphere 2 to prevent rotation of the circular suturing cartridge 15 during use. The inner cavity 19 of the circular suturing cartridge 15 is filled to the top of the cartridge 15 with a soft, semi-solid, resilient material exemplified by silicone and the like. After repeated use for suturing training, the used circular suturing cartridge 15 can be disengaged from the diamond-shaped receptacle 4 and replaced with a fresh circular suturing cartridge 15. Alternatively, the suturing cartridge may be formed into an elliptical shape or a tear-drop shape or an asymmetrical amoeboid shape.

It is within the scope of the present disclosure to use different types of soft, semi-solid, resilient material to fill the plurality of suturing cartridges 12, 15. For example, two semi-solid, resilient materials may be used wherein the circular suturing cartridge 15 is filled with a stiffer semi-solid, resilient material while the diamond-shaped suturing cartridges 12 are filled with a softer semi-solid, resilient material. The stiffer semi-solid, resilient material provides more resistance and grip to suturing instruments during their insertion/withdrawal into/from the circular suturing cartridge 15 while the softer semi-solid, resilient material provides less resistance and grip to suturing instruments during their insertion/withdrawal into/from the diamond-shaped suturing cartridges 12. For example, three semi-solid, resilient materials may be used wherein the circular suturing cartridge 15 is filled with a stiffer semi-solid, resilient material while some of the diamond-shaped suturing cartridges 12 are filled with a less-stiff semi-solid, resilient material, and the remaining diamond-shaped suturing cartridges 12 are filled with a softer semi-solid, resilient material. Accordingly, the user will experience more resistance and grip to suturing instruments during their insertion/withdrawal into/from the circular suturing cartridge 15, and less resistance during their insertion/withdrawal of suturing instruments into/from the diamond-shaped suturing cartridges 12 with the less-stiff semi-solid, resilient material, and even less resistance during their insertion/withdrawal of suturing instruments into/from the diamond-shaped suturing cartridges 12 with the softer semi-solid, resilient material. It is also within the scope of the present invention to provide a thin layer of a polymeric film over top of the soft semi-solid, resilient material contained within the cartridges 12, 15 for the purpose of simulating a serous membrane encasing an organ in order to provide an initial resistance to penetration of suturing instruments that is different from the pressure encountered after the suturing instruments have penetrated a serous membrane.

It is to be noted that each receptacle 3, 4 may additionally cooperate with at least one pressure sensor and/or one vibration sensor for detection of pressures and/or vibrations generated by suturing instrument movements into and within a suturing cartridge 15, 12 (respectively) demountably engaged in the receptacle 3, 4.

It is essential that a medical trainee develops competence in the performance of a variety of different suturing techniques since more than one suturing process is often required to complete a surgical procedure. For example, a trainee must learn to perform interrupted and continuous over-and-under sutures, interrupted and continuous subcuticular sutures, interrupted and continuous horizontal mattress sutures, interrupted and continuous vertical mattress sutures, interrupted and continuous Lembert sutures, Cushing sutures, everting sutures, lock-stitch sutures, Halsted sutures, Connell sutures, purse-string sutures, and the like.

The electronic components enable a trainee and their instructor to interact with the apparatus 50 prior to, during, and after completion of one or more suturing exercises. As shown in FIG. 1, the apparatus 50 may have a user interface 7 with an LCD 8 with two command buttons 9. One of the buttons 9 is used to start and advance a training program through a series of steps pertaining to performance of a selected suturing task. The other of buttons 9 is used to reset the training exercise, or to select a new suturing training exercise. For example, one of the LED lights 5 disposed about a receptacle 3, 4 may emit an orange or yellow light for example, a second of the LED lights disposed about the selected receptacle 3, 4 may emit a green light indicating the location within the selected receptacle 3, 4 wherein a suture throw is to be initiated while the LED light 5 opposite the LED light emitting the green light, may emit a red light to indicate the location within the selected receptacle 3, 4 wherein the suture throw is to be completed. It is optional for the fourth LED light 5 disposed about the selected receptacle to emit a fourth colour corresponding to an angle of insertion for initiating the suture throw.

The microcontroller is interactive with a variety of software programs for training and monitoring performance of various types of suturing techniques performed on one or more of the suturing cartridge(s) 12, 15. An example of a simple software program may comprise a set of instructions to perform a selected suturing technique on a selected cartridge 12, 15, for example with a series of, for example, eight insertion/withdrawal steps (also commonly referred to as "throws"). A more advanced software program may comprise a sequential set of instructions to perform a first selected suturing technique on a first selected cartridge 12, 15, followed by a requirement to perform a second selected suturing technique on a second selected cartridge 12, 15, and if so desired a third selected suturing technique (and optionally, additional selected suturing technique) on a third selected cartridge 12, 15 (and optionally, additionally selected cartridges). Another example of suitable software may comprise a program subroutine for each of the suturing techniques listed above plus a program subroutine for random selection of a specific suturing technique, plus a program subroutine for an input from a user to select a number of suturing techniques to be performed in a training exercise. The selection of the suturing techniques and their sequence of presentation is randomly generated by the software program. The software programs may receive and process data detected by the pressure sensors and/or vibration sensors during performance of a suturing technique, for example, pressure/vibration caused by insertion of a suturing instrument into and withdrawal from the soft, semi-solid, resilient material contained within the cartridge, sideway pressure caused by movement of the suturing instrument within the soft, semi-solid, resilient material, spacing apart of the insertions/withdrawals of the suturing instrument during performance of a suturing technique, angles of insertion and withdrawals, and the number of insertions/withdrawals made during the performance of the suturing technique. If the number of insertions/withdrawals, the pressures applied during the insertions, the spacing of the insertions, and angles of insertion/withdrawals are within the tolerance levels written into the software subroutines, then the LEDs positioned around the target cartridge may display a green light. If the sensors indicate that one or more of the insertions/withdrawals during performance of a suturing technique have been made outside of the programmed tolerance levels, then the LEDs situated around the cartridge may display a red light. It is an option for the LEDs to display a yellow or orange light if the sensors indicate that an insertion/withdrawal is approaching one or more tolerance levels. The software programs also record the time taken to perform a selected suturing technique, and also, the total time taken to perform a selected sequence or randomly generated sequence of suturing techniques. The software programs may additionally have subroutines to display, record, and optionally store a finished suture produced within a target cartridge by a user during their performance of a suturing technique along with related data exemplified by: (i) pressures exerted during each insertion/withdrawal step, (ii) spacing of the insertion/withdrawal steps, and (ii) time taken to perform the suturing technique.

The invention claimed is:

1. An apparatus for training a practitioner in performance of suturing techniques, the apparatus comprising:
   a first suturing cartridge comprising a first container for receiving therein a soft, semi-solid, resilient material, wherein the outer wall of the first container has a continuous curvilinear shape;
   a second suturing cartridge comprising a second container for receiving therein the soft, semi-solid, resilient material, wherein the outer wall of the second container has a geometric shape defined by at least three intersecting linear planes;
   a suturing cartridge presentation display having a first receptacle for demountably engaging therein the first suturing cartridge and a second receptacle for demountably engaging therein the second suturing cartridge, wherein the rim of the first receptacle is a mirror image of the curvilinear shape of the outer wall of the first suturing cartridge, and wherein the rim of the second receptacle is defined by a mirror image of the geometric shape of the outer wall of the second suturing cartridge;
   said suturing cartridge presentation display having a first plurality of light-emitting diodes mounted therein wherein each of said first plurality of light-emitting diodes is equidistantly spaced around and adjacent to the rim of the first receptacle, wherein each of said first plurality of light-emitting diodes emits a first light in response to a first signal and a second light in response to a second signal directed to said light-emitting diode;
   said suturing cartridge presentation display having a second plurality of light-emitting diodes mounted therein wherein each of said second plurality of light-emitting diodes is adjacent to a corner of the geometric shape defining the rim of the second receptacle, wherein each of said second plurality of light-emitting diodes emits a first light in response to a first signal and a second light in response to a second signal directed to said light-emitting diode;
   a microprocessor for communicating with the first plurality and the second plurality of light emitting diodes, a graphical user interface, and at least one software program for cooperating with the microprocessor to sequentially send (i) a first set of a first signal and a second signal separately to two of the first plurality of light-emitting diodes, followed by (ii) a second set of a first signal and a second signal separately to two of the second plurality of light-emitting diodes; and
   a housing for mounting therein the suturing cartridge presentation display, the microprocessor, and the graphical user interface.

2. The apparatus of claim 1, wherein each of the first plurality of light-emitting diodes and/or each of the second plurality of light-emitting diodes emits a third light in response to a third signal, and optionally, a fourth light in response to a fourth signal.

3. The apparatus of claim 1, wherein the suturing cartridge presentation display additionally has one or more first receptacles for demountably engaging therein an additional one or more of the first suturing cartridge, each of the one or more first receptacles associated with a plurality of light-emitting diodes provided therefore in the suturing cartridge presentation display.

4. The apparatus of claim 1, wherein the suturing cartridge presentation display additionally has one or more second receptacles for demountably engaging therein an additional one or more of the second suturing cartridge, each of the one or more second receptacles associated with a plurality of light-emitting diodes provided therefore in the suturing cartridge presentation display.

5. The apparatus of claim 1, wherein each of the plurality of first light-emitting diodes and each of the second plurality of light-emitting diodes emits a green light in response to the first signal and emits a red light in response to the second signal.

6. The apparatus of claim 2, wherein each of the first plurality of light-emitting diodes and each of the second plurality of light-emitting diodes emits one of a yellow light or an orange light in response to the third signal and optionally, emits the non-emitted color of the yellow light and the orange light in response to the fourth signal.

7. The apparatus of claim 1, wherein the first receptacle is provided with a first pressure sensor that sends a first pressure signal to the microprocessor when a first pressure is applied to the first suturing cartridge thereby causing the microprocessor to send a first or second signal to one of the first plurality of light-emitting diodes.

8. The apparatus of claim 7, wherein the first pressure sensor additionally sends a second pressure signal to the microprocessor when a second pressure is applied to the first suturing cartridge thereby causing the microprocessor to send a first or second signal to another one of the first plurality of light-emitting diodes.

9. The apparatus of claim 1, wherein the second receptacle is provided with a second pressure sensor that sends a first pressure signal to the microprocessor when a first pressure is applied to the second suturing cartridge thereby causing the microprocessor to send a first or second signal to one of the second plurality of light-emitting diodes.

10. The apparatus of claim 9, wherein the second pressure sensor additionally sends a second pressure signal to the microprocessor when a second pressure is applied to the first suturing cartridge thereby causing the microprocessor to send a first or second signal to another one of the second plurality of light-emitting diodes.

11. The apparatus of claim 1, wherein the first suturing cartridge has an outer shape in the form of a circle or an ellipse or a toroid or an amoeboid.

12. The apparatus of claim 1, wherein the second suturing cartridge has an outer shape in the form of one of a diamond or a square or a rectangle or a parallelogram or a triangle.

13. The apparatus of claim 1, wherein the housing has a transparent coverplate, said coverplate having at least one surgical port for inserting therethrough an endoscopy instrument.

14. The apparatus of claim 1, wherein the housing has side surfaces and a bottom surface comprising wood or metal or plastic or a combination thereof.

15. The apparatus of claim 1, wherein the suturing cartridge presentation display is formed into a topographical representation of a mammalian organ.

16. The apparatus of claim 15, wherein the mammalian organ is one of a heart, a lung, a stomach, a liver, a gall bladder, a pancreas, a kidney, a bladder, a urethra, an ovary, a fallopian tube, and a uterus.

17. The apparatus of claim 15, wherein the mammalian organ is a human organ.

* * * * *